United States Patent [19]

Emery et al.

[11] 3,950,512
[45] Apr. 13, 1976

[54] ANIMAL VACCINES

[75] Inventors: Jerrell Bemis Emery, Chalfont; James Long Bittle, Doylestown, both of Pa.

[73] Assignee: Pitman-Moore, Inc., Washington Crossing, N.J.

[22] Filed: Feb. 6, 1975

[21] Appl. No.: 547,430

Related U.S. Application Data

[63] Continuation-in-part of Ser. No. 274,940, July 25, 1972, abandoned, which is a continuation-in-part of Ser. No. 94,570, Dec. 2, 1970, abandoned.

[52] U.S. Cl. .................... 424/89; 195/1.3; 424/92
[51] Int. Cl.² A61K 39/02; A61K 39/18; A61K 39/34
[58] Field of Search .................. 424/89, 92; 195/1.3

[56] References Cited
OTHER PUBLICATIONS

Binn et al., P.S.E.B.M. 126: 140–145 (1967), "Viruses Recovered from Laboratory Dogs with Respiratory Disease".
Rosenberg et al., FEDN. Proc. 29, 636, (Apr, 15, 1970), "A Canine Parainfluenza Virus, Its Role in Respiratory Disease in Dogs."
Bittle et al., J.A.V.M.A., 156, (12 pt.1): 1771–1773, June 15, 1970, "The Epizootiology of Canine Parainfluenza".
Binn et al., J.A.V.M.A. 156, (12, pt.1): 1774–1777, June 15, 1970, "Comments on Epizootiology of Parainfluenza SV–5 in Dogs".
Appel et al. J.A.V.M. 156, (12, pt.1): 1778–1781, June 15, 1970, "SV–5–like Parainfluenza in Dogs."
Tribe et al., J. Small Anim. Pract. 14, (5): 251–255, May, 1973, "Protection of Dogs Against Canine Hepatitis With Toronto, A26/61 Virus, (Kennel Cough Isolate), Hexon Antigen."

*Primary Examiner*—Shep K. Rose
*Attorney, Agent, or Firm*—Salvatore R. Conte

[57] ABSTRACT

An immunizing vaccine for use against kennel cough in dogs comprising live, non-pathogenic, canine parainfluenza virus as the sole immunogenic agent or in combination with either or both of live, non-pathogenic, canine adenovirus Type 2, and inactivated *Bordetella bronchisepticus* bacteria.

24 Claims, No Drawings

ANIMAL VACCINES

CROSS-REFERENCE TO RELATED APPLICATIONS

This is a continuation-in-part of our copending application Ser. No. 274,940, filed July 25, 1972, now abandoned which in turn is a continuation-in-part of application Ser. No. 94,570, filed Dec. 2, 1970, now abandoned.

BACKGROUND OF THE INVENTION

Laryngotracheitis is an inflammation of larynx and trachea which, when it occurs in dogs, is known commonly as "kennel cough". The main symptom is cough manifested by a short, dry "hack" or by a series of such coughs. When most severe, the cough may be paroxysmal, and the infection involves the entire respiratory tract, often producing a pneumonia. The cough is also characterized as being deep, persistent, non-productive and generally accompanied by running eyes and nose. The temperature may be normal although generally it is elevated. The onset of the disease is sudden and without preliminary signs. Since the disease is very contagious, infected dogs should be isolated so as not to affect entire populations. The disease produces major economic losses to kennel owners, and while not usually fatal it may so weaken dogs as to produce serious effects from other diseases. Today, treatment of the disease includes the prophylactic use of distemper hepatitis antiserum to prevent those diseases from complicating the original infection together with antibiotics, such as chloramphenicol, chlortetracycline and oxytetracycline to control bacterial involvement. There is, however, no vaccine presently available which is used to immunize dogs against the causative agents of kennel cough.

DESCRIPTION OF THE INVENTION

An object of this invention is to provide a vaccine useful against kennel cough in dogs, which vaccine is immunogenic and non-pathogenic to the subject to be immunized.

Another object of this invention is to provide such a vaccine comprising live, non-pathogenic, canine parainfluenza (CPI) virus as the sole immunogenic agent.

An additional object of the invention is to provide such a vaccine comprising live, non-pathogenic canine parainfluenza (CPI) virus and live, non-pathogenic canine adenovirus Type 2.

A further object of this invention is to provide such a vaccine comprising live, non-pathogenic, CPI virus in combination with either or both of live, nonpathogenic, canine adenovirus Type 2 and inactivated *Bordetella bronchisepticus* bacteria.

The three main causative agents found to be associated with kennel cough are two viral agents, canine parainfluenza virus and canine adenovirus Type 2, and the bacteria, *Bordetella bronchisepticus* (e.g., see L. Binn et al., P. S. E. B. M., 1967, 126:140; R. A. Crandell et al., Am J. Vet. Res., 1968, 29:241; J. Ditchfield et al., Canad. Vet. Jour., 1962, 3:238; and T. Yamamoto, 1966, Canad. J. of Microb., 12:303; M. J. G. Appel et al., J. A. V. M. A., 1970, 156:1778). The adenovirus described by Ditchfield et al. and Yamamoto is the Toronto A26/61 strain. This strain is an adenovirus Type 2 (see G. A. Fairchild et al., Am. J. Vet. Res., 1969, 30:923 and 30:1187). When the live virulent form of these three agents is administered to susceptible dogs, the clinical symptoms of kennel cough are exhibited, generally within 2 to 6 days following administration. The administration of these three live virulent agents can thus be used as a method of challenging a potential vaccine to test its immunogenic properties against same. In our tests, we have found the vaccines of this invention to be effective in immunizing susceptible dogs when challenged with infectious doses of the three agents. From the results of these tests, it is contemplated that our vaccine may be used to significantly control the incidence of kennel cough in dogs.

In addition, the vaccine comprising canine adenovirus Type 2 (CAV 2) when administered in effective amounts either alone or in conjunction with the other vaccines described herein, will immunize dogs against infectious canine hepatitis (ICH). This disease is a serious one involving the liver and kidneys and is frequently fatal. It is caused by the virus designated as canine adenovirus Type 1 (CAV 1) which is different from CAV 2. Unfortunately a live attenuated virus vaccine prepared from the Type 1 virus is not suitable for immunization purposes for a variety of reasons. The primary disadvantage arises from the side effects caused by replication of the virus at sites remote from the liver and kidneys. For example, corneal opacities are frequently encountered in dogs vaccinated with a vaccine prepared from a live attenuated CAV 2 virus. A killed CAV 2 virus vaccine is effective for such a short period of time as to be essentially useless. In accordance with the present invention, in general, live CAV 2 virus vaccines sufficient to immunize against the clinical symptoms caused by CAV 1, i.e. kennel cough, will be sufficient to immunize against ICH. Of course, the vaccines of the invention comprise the live viruses in a pharmaceutically acceptable medium and may be administered parenterally or intra-nasally.

The two viral agents, CPI virus and canine adenovirus Type 2, can be obtained from dogs infected with laryngotracheitis according to methods of isolation and identification described in the literature (e.g., see L. Binn et al., P. S. E. B. M., 1967, 126:140; R. A. Crandell et al., Am. J. Vet. Res., 1968, 29:241; J. Ditchfield et al., Canad. Vet. Jour., 1962, 3:238; and T. Yamamoto, Canad. J. of Microb., 1966, 12:303). The *Bordetella bronchisepticus* bacteria is deposited with the American Type Culture Collection as ATCC 4617.

In preparing the vaccines of this invention, the virulent CPI virus and canine adenovirus Type 2 are each propagated in animal tissue cultures until both viruses are rendered non-pathogenic, i.e., the viruses are rendered avirulent. The CPI virus is capable of propagation in a wide variety of tissue culture systems, such as, for example, chick embryo, duck embryo, porcine kidney, porcine testes, embryonic bovine kidney, feline kidney, canine kidney and monkey kidney; and also in established cell lines, such as, for example, Madin Darby bovine kidney (MDBK), Madin Darby canine kidney (MDCK) and Serum Institute rabbit cornea (SIRC). For the propagation of the canine adenovirus Type 2, kidney tissue cultures are preferred, particularly those derived from bovine and the dog, since this virus does not seem to favorably replicate in other animal tissue culture systems as does the CPI virus. Attenuation of each virus is accomplished by standard serial passages including terminal dilution passage techniques wherein a sufficient number of passages in a susceptible tissue culture is employed until the virus is rendered non-pathogenic without loss of immunogenicity. A vaccine prepared therefrom will stimulate an immune response in dogs susceptible to disease without producing the clinical symptoms normally due to the virulent agent to any significant degree. The propagation can be conducted in the same or different tissues as those employed in the preceding passage.

The passage time intervals should be such as to sufficiently allow the virus to replicate between passages, and incubation temperatures are preferably maintained from 30° to 38°C. The optimum passage time interval depends on the particular culture system and temperature being employed. In any event, whether or not sufficient replication of the virus has occurred can readily be determined by standard techniques such as the hemadsorption technique described by A. SHELOKOV, P.S.E.B.M. 1958, 97:802 which is particularly utilizable for the CPI virus, or by cytopathic observations, such as by allowing the virus to grow during a particular passage prior to the point where a gross cytopathic effect can be observed while continuing incubation.

The preferred method of propagation utilizes canine kidney cells, particularly the MDCK continous cell line. For example, for kennel cough vaccine purposes, about at least 15 and preferably from about 20 to about 45 passages from isolation through dog kidney tissue cultures of the viruses are made at approximately three-day intervals and at incubation temperatures of 30°-38°C. For ICH vaccine purposes, a somewhat lower number of passages of the order of 10–25 will ordinarily be sufficient to render the CAV 2 virus essentially non-pathogenic with respect to its ICH properties. It is preferred, however, to utilize the higher passage material since this will benefit the production of a favorable immune response to kennel cough as well.

With regard to the bacterial component of the subject vaccines, the live *Bordetella bronchisepticus* is subjected to conventional chemical or physical inactivation procedures whereby the organism is rendered non-viable but still retentive of its antigenic properties. Such procedures, which are the same type which are useful with viruses are described in the ANNALS OF THE NEW YORK ACADEMY OF SCIENCES, 1960, Vol. 83, pp. 513–760.

For purposes of this invention, the final vaccine product should contain an amount of each avirulent viral component sufficient to stimulate an immune response in disease-susceptible dogs and still be non-pathogenic. Although lower titres may be employed, we recommend a minimum titre for each of the live attenuated viruses in the final vaccine product of at least 100 $TCID_{50}$ per ml and preferably from about $10^4$ to about $10^6$ $TCID_{50}$ per ml. The bacterial concentration should be from about 100,000 ($10^5$) to about 1 billion ($10^9$) inactivated bacterial organisms per ml. Calculation of bacterial titers is usually accomplished by standard techniques prior to inactivation of the bacteria.

The viral preparations produced by this invention may be diluted with water to adjust their potency, and they may have added to them stabilizers, such as dextrose and lactose, or other non-toxic substances. The viral preparations may also be desiccated, e.g., by freeze drying, for storage purposes or for subsequent formulation into liquid vaccines. Stabilizers useful in the freeze drying of viruses are described in W. A. Rightsel et al., Cryobiology, 1967, 3:423 and D. Greiff et al., *Advances in Freeze Drying*, L. Rey, Ed., pp. 103–122, Hermann, Paris, 1966. In addition, the vaccines may be utilized in a mixture with other immunogenic or therapeutic vaccines for administration to dogs.

The subject vaccines are administered to dogs by various routes, including intramuscular, intravenous, subcutaneous, intratracheal and intra-nasal. For maximum effectiveness, vaccines comprising all three agents, namely, (1) the live, non-pathogenic, CPI virus, (2) the live, non-pathogenic, canine adenovirus Type 2 and (3) the inactivated *Bordetella bronchisepticus*, are preferably employed for immunogenic purposes against kennel cough although vaccines comprising the viral agent (1) alone or in combination with the viral agent (2) or in combination with the bacterial agent (3) may also be utilized. Of course, administration of the CAV 2 virus vaccine alone is effective where immunization against ICH is sought.

EXAMPLE I

A sample of live virulent CPI virus obtained according to the procedure described in L. Binn et al., P. S. E. B. M., 1967, 126:140 was passed in roller tube cultures of MDBK continuous cell line. Passages were conducted by transferring 0.2 ml. aliquots of fluids harvested from infected MDBK roller tube cultures to additional MDBK cultures containing 2 ml. of a maintenance medium composed of Eagles MEM supplemented with 2% fetal calf serum. Inoculated cultures were incubated at 30°C. for 3 days at which time the monolayer of cells was frozen and thawed to release intracellular virus and the media from the inoculated cultures containing virus and cell debris were pooled for passage into additional cultures. Thirty such passages were conducted. The titre of this pooled vaccine finally obtained was found to be $10^{5.4}$ $TCID_{50}$ per ml.

EXAMPLE II

Live virulent canine adenovirus Type 2 obtained according to J. Ditchfield et al. Canad. Vet. Jour., 1962, 3:238, and already having had about nine passages through primary dog kidney tissue culture, was passed in roller tube cultures of MDBK continuous cell line. The initial four passages were conducted by inoculating 0.2 ml. aliquots of virus laden fluids from infected cultures at the time of preparation and prior to the establishment of confluent monolayers. Cultures were incubated at 35° C. Complete cytopathic effects (90–100% of cells destroyed) were noted in the inoculated cultures from 4 to 9 days after inoculation. For the 5th through 29th passages, fully monolayered cultures of MDBK cells were inoculated in 0.2 ml. aliquots per tube with fluids obtained from the previous passage. Incubation of these cultures was conducted at 30°C. in a roller drum apparatus. Partial or complete cytopathic effects (50% to 100% of cells destroyed) were noted from 2–5 days after inoculation at which time the virus laden fluids were harvested and pooled. The titre of the pooled vaccine was found to be $10^{7.0}$ $TCID_{50}$ per ml.

EXAMPLE III

Virulent strains of *Bordetella bronchisepticus* (ATCC 4617) were thawed from frozen stock cultures and transferred to flasks of NZ Case broth medium. These seed culture flasks were incubated 48 hours at 37°C. after which they were examined for purity and portions were transferred to culture flasks containing 400 ml. amounts of NZ Case broth medium. An equal number of flasks were inoculated with the bacteria. These flasks were incubated at 37°C. until the cell count of viable bacteria reached at least one billion organisms per ml. 48 hours was required. Formaldehyde was added to the organisms in sufficient quantity to yield 0.25% concentration of formaldehyde and the treated material was incubated at 37°C. for 3 days. After this treatment the formaldehyde was neutralized with sodium hydroxide and the pH adjusted to 7.3. The bacterial suspension then incubated at 37°C. and for additional 24 hours and dispensed into final container bottles. Testing of the final inactivated bacterial preparation showed it to be sterile. Prior to inactivation the titer equaled about $10^6$ inactivated bacteria per ml.

EXAMPLE IV

Equal parts of the live, attenuated CPI virus vaccine obtained from Example I and the live, attenuated canine adenovirus Type 2 vaccine obtained from Example II were mixed and 1 ml. aliquots administered to two dogs by the intra-nasal route and to two dogs by the parenteral route. Four dogs were retained as unvaccinated controls. The dogs were observed for 18 days for evidence of clinical disease at which time they were challenged by administering approximately 0.5 ml. of a mixture of virulent CPI virus and canine adenovirus Type 2 by the intra-nasal route. 24 hours after the initial viral challenge the dogs were given 0.2 ml. of virulent Bordetella bronchisepticus bacteria into each nostril. The dogs were observed for 11 days for clinical disease at which time they were sacrificed for pathological examination.

No clinical disease or symptoms of kennel cough were noted in any of the dogs after vaccination. Clinical disease was not present in the two dogs vaccinated by the intra-nasal route or the two dogs vaccinated by the parenteral route after challenge with the two virulent viruses and bacteria. Three to six days after being challenged, all four of the non-vaccinated control dogs exhibited clinical disease, exhibiting symptoms such as febrile response, running eyes and nose and coughing. Upon post mortem conducted 11 days after challenge, no gross lesions were observed in any of the four vaccinated dogs, however, significant gross lesions were observed in the four unvaccinated control dogs. These lesions consisted of discoloration of the lungs with marked areas of pneumonic consolidation around the periphery of the lobes. The mediastinal and bronchial lymph nodes were swollen and mucoid deposits were present in the nasal turbinates. The nasal mucosa was markedly thickened and hyperemic.

EXAMPLE V

Two dogs were given 1 ml. of a vaccine consisting of equal parts of (1) the live, attenuated CPI virus vaccine of Example I, (2) the live, attenuated canine adenovirus Type 2 preparation of Example II, and (3) the inactivated Bordetella bronchisepticus preparation of Example III by the parenteral route. Two dogs were retained as unvaccinated controls. The dogs were observed for 18 days for evidence of clinical disease at which time they were challenged with virulent virus and bacteria as described in Example IV. Eleven days after challenge the dogs were sacrificed for pathological examination.

No clinical disease or symptoms of kennel cough were noted in the two vaccinated dogs either after vaccination or after challenge with the two virulent viruses and bacteria. Symptoms of clinical disease were noted in the two control dogs similar to that described in Example IV. No significant lesions were observed in either vaccinated dog upon post mortem, however significant lesions, as described in Example IV, were observed in both unvaccinated control dogs.

Similar immunization results are also obtained when non-infected dogs are given 1 ml s.c. of a vaccine consisting of equal parts of the CPI virus vaccine of Example I and the inactivated bacterial preparation of Example III.

EXAMPLE VI

The live CAV 2 virus recited in Example II having had a total of ten passages through primary dog kidney tissue culture resulted in a live attenuated virus vaccine having a titre of $10^{-6.7}$ per ml.

This vaccine was used to vaccinate dogs intramuscularly at a dosage level of 1 ml. per dog as follows:

A group of eleven dogs, 5 months old and weighing about 9 kg. each, was chosen. One group of seven litter mates from this main group was inoculated as indicated above, another group of two was not vaccinated but was housed with the inoculated seven, and a third group of two served as untreated controls and was segregated from the first two groups.

No clinical symptoms of ICH were noted in any of the vaccinated dogs following vaccination.

Antibody titres against both CAV 2 and ICH were obtained on blood sera of all animals at 2 weeks and 4 weeks following inoculation and compared to the pre-inoculation level using the standard serum neutralization test (Fieldsteel, A. H. and Emery, J. B., P.S.E.B.M., 1954, 86:819).

TABLE I

| Dog No. | Antibody Responses* | | | | | | ICH Challenge Response |
|---|---|---|---|---|---|---|---|
| | CAV 2 | | | ICH | | | |
| | Pre | 2 Wk. | 4 Wk. | Pre | 2 Wk. | 4 Wk. | |
| A | 0 | 3,200 | 3,200 | 0 | 100 | 1,000 | (No |
| B | 0 | 320 | 3,200 | 0 | 200 | 3,200 | Clinical |
| C | 0 | 500 | 3,200 | 0 | 50 | 500 | Symptoms) |
| D | 0 | 320 | 2,000 | 0 | 32 | 320 | " |
| E | 0 | 3,200 | 3,200 | 0 | 320 | 2,000 | " |
| F | 0 | 2,000 | 3,200 | 0 | 320 | 3,200 | " |
| G | 0 | 320 | 3,200 | 0 | 320 | 500 | " |
| Contact | | | | | | | |
| H | 0 | 2,000 | 3,200 | 0 | 63 | 3,200 | " |
| I | 0 | 1,000 | 20,000 | 0 | 320 | 3,200 | " |
| Challenge | | | | | | | |

TABLE I-continued

| Dog No. | Antibody Responses* | | | | | | ICH Challenge Response |
|---|---|---|---|---|---|---|---|
| | CAV 2 | | | ICH | | | |
| | Pre | 2 Wk. | 4 Wk. | Pre | 2 Wk. | 4 Wk. | |
| J | 0 | — | 0 | 0 | — | 0 | Febrile 2nd day Dead 5th day |
| K | 0 | — | 0 | 0 | — | 0 | Febrile 2nd day Dead 3rd day |

*Reciprocal of 50% serum dilution endpoint

As can be seen from Table I, antibody developed to both viral antigens in dogs receiving the inoculation. Interestingly, those dogs not inoculated but housed with the treated animals also developed immunity. The controls produced no antibodies to ICH or CAV 2 virus antigen and succumbed to the ICH challenge. Infection was confirmed by histopathological examination.

EXAMPLE VII

The procedure of Example II was repeated except that the virus propagation was terminated after the 15th passage through MDBK cell line instead of carrying it through 29 passages. A vaccine having a titre of $10^{-6.7}$ per 1 ml. is thus obtained. This was combined with a CPI virus vaccine prepared in accordance with Example I. 1 ml. or 0.5 ml. of the mixed vaccine was administered either intramuscularly or intra-nasally (aerosol) as indicated to each of the indicated dogs (8 kg. each). Antibody response was measured on serum samples taken just prior to and three weeks after vaccination utilizing the serum neutralization test described in Example VI. Table II summarizes the results:

TABLE II

| Dog No. | Vaccination Route | Antibody Response* | | | |
|---|---|---|---|---|---|
| | | CAV 2 Virus | | ICH Virus | |
| | | Pre | Post | Pre | Post |
| 1 | I.M.(1 ml.) | 0 | 320 | 0 | 32 |
| 2 | I.M.(1 ml.) | 0 | 320 | 0 | 50 |
| 3 | Aerosol(0.5 ml.) | 0 | 320 | 0 | 32 |
| 4 | Aerosol(0.5 ml.) | 0 | 3200 | 0 | 200 |
| 5 | Control | 0 | 0 | 0 | 0 |
| 6 | Control | 0 | 0 | 0 | 0 |
| 7 | Control | 0 | 0 | 0 | 0 |
| 8 | Control | 0 | 0 | 0 | 0 |

*Reciprocal of 50% serum dilution endpoint.

As can be seen from Table II, the vaccinates developed antibody to both CAV 2 and ICH antigens regardless of whether the combination vaccine was administered by the aerosol technique or by the intramuscular route. These vaccinates would be immune to ICH virus challenge since ICH antibody titre in excess of 1:10 have been shown to be protective.

EXAMPLES VIII

The procedure of Example VII is followed except that the CAV 2 vaccine is not combined with CPI virus vaccine and it is administered subcutaneously to dogs weighing about 11 kg. Table III shows the antibody production against CAV 2 virus and ICH virus.

TABLE III

| Dog No. | Vaccination Route | Antibody Response* | | | | | |
|---|---|---|---|---|---|---|---|
| | | CAV 2 VIRUS | | | ICH VIRUS | | |
| | | Pre Inoc. | 14 Day Post | 21 Day Post | Pre Inoc. | 14 Day Post | 21 Day Post |
| 1 | S.Q. | 0 | 250 | 250 | 0 | 32 | 50 |
| 2 | S.Q. | 0 | 250 | 400 | 0 | 80 | 40 |
| 3 | S.Q. | 0 | 400 | 500 | 0 | 64 | 80 |
| 4 | Control | 0 | 0 | 0 | 0 | 0 | 0 |
| 5 | Control | 0 | 0 | 0 | 0 | 0 | 0 |
| 6 | Control | 0 | 0 | 0 | 0 | 0 | 0 |

*Reciprocal of 50% serum dilution endpoint

As can be seen, the CAV 2 vaccine of the invention produces a strong antibody response to the ICH virus, sufficient to confer immunity to challenge.

EXAMPLE IX

1 Ml of the live attenuated CPI virus vaccine obtained from Example I is administered to two dogs by the intranasal route and to two dogs by the parenteral route (I.M.). Four dogs are retained as unvaccinated controls. No clinical evidence of kennel cough is observed for 18 days at which time the vaccinated dogs and the controls are challenged by administering approximately 0.5 ml of a mixture of virulent CPI virus and canine adenovirus Type 2 by the intranasal route. Twenty-four hours later the eight dogs are given 0.2 ml of virulent *Bordetella bronchisepticus* into each nostril. The dogs are observed for 11 days for clinical disease symptoms of kennel cough at which time they are sacrificed for pathological examination. No clinical disease or symptoms of kennel cough are noted in the four vaccinated dogs either after vaccination or after challenge. Typical clinical disease symptoms of kennel cough are observed in the unvaccinated controls similar to those described in Example IV.

EXAMPLE X

The procedures of Examples I and II are followed, except that an MDCK cell line is substituted for the MDBK cell line used therein to yield similar CPI and CAV 2 vaccines, respectively.

What is claimed is:

1. A vaccine useful in immunizing dogs against kennel cough comprising at least 100 $TCID_{50}$ per ml each of live attenuated canine parainfluenza virus and live attenuated canine adenovirus Type 2 in a physiologically acceptable carrier suitable for parenteral or intranasal administration, each of said viruses being attenuated by a sufficient number of serial passages in susceptible tissue culture until the virus is rendered nonpathogenic without loss of immunogenicity.

2. A vaccine useful in immunizing dogs against kennel cough comprising from about $10^4$ to about $10^6$ $TCID_{50}$ per ml each of live attenuated canine parainfluenza virus and live attenuated canine adenovirus Type 2 in a physiologically acceptable carrier suitable for parenteral or intranasal administration, each of said viruses being attenuated by at least 15 serial passages in susceptible tissue culture to render the virus non-pathogenic without loss of immunogenicity.

3. A vaccine useful in immunizing dogs against kennel cough comprising from about $10^4$ to about $10^6$ $TCID_{50}$ per ml each of live attenuated canine parainfluenza virus and live attenuated canine adenovirus Type 2 in a physiologically acceptable carrier suitable for parenteral or intranasal administration, each of said viruses being attenuated by from about 20 to about 45 serial passages in canine kidney tissue culture to render the virus non-pathogenic without loss of immunogenicity.

4. A method of immunizing dogs against kennel cough which comprises parenterally or intranasally administering to a susceptible dog at least 100 $TCID_{50}$ per ml each of live attenuated canine parainfluenza virus and live attenuated canine adenovirus Type 2 in a physiologically acceptable carrier each of said viruses being attenuated by a sufficient number of serial passages in susceptible tissue culture until the virus is rendered non-pathogenic without loss of immunogenicity.

5. A method of immunizing dogs against kennel cough which comprises parenterally or intranasally administering to a susceptible dog from about $10^4$ to about $10^6$ $TCID_{50}$ per ml each of live attenuated canine parainfluenza virus and live attenuated canine adenovirus Type 2 in a physiologically acceptable carrier, each of said viruses being attenuated by at least 15 serial passages in susceptible tissue culture to render the virus non-pathogenic without loss of immunogenicity.

6. A method of immunizing dogs against kennel cough which comprises parenterally or intranasally administering to a susceptible dog from about $10^4$ to about $10^6$ $TCID_{50}$ per ml each of live attenuated canine parainfluenza virus and live attenuated canine adenovirus Type 2 in a physiologically acceptable carrier, each of said viruses being attenuated by from about 20 to about 45 serial passages in canine kidney tissue culture to render the virus non-pathogenic without loss of immunity.

7. A vaccine useful in immunizing dogs against kennel cough comprising from about $10^5$ to about $10^9$ inactivated *Bordetella bronchisepticus* bacteria per ml and at least 100 $TCID_{50}$ per ml each of live attenuated canine parainfluenza virus and live attenuated canine adenovirus Type 2 in a physiologically acceptable carrier suitable for parenteral or intranasal administration, each of said viruses being attenuated by a sufficient number of serial passages in susceptible tissue culture until the virus is rendered nonpathogenic without loss of immunogenicity.

8. A vaccine useful in immunizing dogs against kennel cough comprising from about $10^5$ to about $10^9$ inactivated *Bordetella bronchisepticus* bacteria per ml and from about $10^4$ to about $10^6$ $TCID_{50}$ per ml each of live attenuated canine parainfluenza virus and live attenuated canine adenovirus Type 2 in a physiologically acceptable carrier suitable for parenteral or intranasal administration, each of said viruses being attenuated by at least 15 serial passages in susceptible tissue culture to render the virus non-pathogenic without loss of immunogenicity.

9. A vaccine useful in immunizing dogs against kennel cough comprising from about $10^5$ to about $10^9$ inactivated *Bordetella bronchisepticus* bacteria per ml and from about $10^4$ to about $10^6$ $TCID_{50}$ per ml each of live attenuated canine prarinfluenza virus and live attenuated canine adenovirus Type 2 in a physiologically acceptable carrier suitable for parenteral or intranasal administration, each of said viruses being attenuated by from about 20 to about 45 serial passages in canine kidney tissue culture to render the virus non-pathogenic without loss of immunogenicity.

10. A method of immunizing dogs against kennel cough which comprises parenterally or intranasally administering to a susceptible dog from about $10^5$ to about $10^9$ inactivated *Bordetella bronchisepticus* bacteria per ml and at least 100 $TCID_{50}$ per ml each of live attenuated canine parainfluenza virus and live attenuated canine adenovirus Type 2 in a physiologically acceptable carrier, each of said viruses being attenuated by a sufficient number of serial passages in susceptible tissue culture until the virus is rendered non-pathogenic without loss of immunogenicity.

11. A method of immunizing dogs against kennel cough which comprises parenterally or intranasally administering to a susceptible dog from about $10^5$ to about $10^9$ inactivated *Bordetella bronchisepticus* bacteria per ml and from about $10^4$ to about $10^6$ $TCID_{50}$ per ml each of live attenuated canine parainfluenza virus and live attenuated canine adenovirus Type 2 in a physiologically acceptable carrier, each of said viruses being attenuated by at least 15 serial passages in susceptible tissue culture to render the virus non-pathogenic without loss of immunogenicity.

12. A method of immunizing dogs against kennel cough which comprises parenterally or intranasally administering to a susceptible dog from about $10^5$ to about $10^9$ inactivated *Bordetella bronchisepticus* bacteria per ml and from about $10^4$ to about $10^6$ $TCID_{50}$ per ml each of live attenuated canine parainfluenza virus and live attenuated canine adenovirus Type 2 in a physiologically acceptable carrier, each of said viruses being attenuated by from about 20 to about 45 serial passages in canine kidney tissue culture to render the virus non-pathogenic without loss of immunogenicity.

13. A vaccine useful in immunizing dogs against kennel cough comprising from about $10^5$ to about $10^9$ inactivated *Bordetella bronchisepticus* bacteria per ml and at least 100 $TCID_{50}$ per ml of live attenuated canine parainfluenza virus in a physiologically acceptable carrier suitable for parenteral or intranasal administration, said virus being attenuated by a sufficient number of serial passages in susceptible tissue culture until the virus is rendered non-pathogenic without loss of immunogenicity.

14. A vaccine useful in immunizing dogs against kennel cough comprising from about $10^5$ to about $10^9$ inactivated *Bordetella bronchisepticus* bacteria per ml and from about $10^4$ to about $10^6$ $TCID_{50}$ per ml of live attenuated canine parainfluenza virus in a physiologically acceptable carrier suitable for parenteral or intranasal administration, said virus being attenuated by at least 15 serial passages in susceptible tissue culture to render the virus non-pathogenic without loss of immunogenicity.

15. A vaccine useful in immunizing dogs against kennel cough comprising from about $10^5$ to about $10^9$ inactivated *Bordetella bronchisepticus* bacteria per ml and from about $10^4$ to about $10^6$ $TCID_{50}$ per ml of live attenuated canine parainfluenza virus in a physiologically acceptable carrier suitable for parenteral or intranasal administration, said virus being attenuated by from about 20 to about 45 serial passages in canine kidney tissue culture to render the virus non-pathogenic without loss of immunogenicity.

16. A method of immunizing dogs against kennel cough which comprises parenterally or intranasally administering to a susceptible dog from about $10^5$ to about $10^9$ inactivated *Bordetella bronchisepticus* bacteria per ml and at least 100 $TCID_{50}$ per ml of live attenuated canine parainfluenza virus in a physiologically acceptable carrier, said virus being attenuated by a sufficient number of serial passages in susceptible tissue culture until the virus is rendered nonpathogenic without loss of immunogenicity.

17. A method of immunizing dogs against kennel cough which comprises parenterally or intranasally administering to a susceptible dog from about $10^5$ to about $10^9$ inactivated *Bordetella bronchisepticus* bacteria per ml and from about $10^4$ to about $10^6$ $TCID_{50}$ per ml of live attenuated canine parainfluenza virus in a physiologically acceptable carrier, said virus being attenuated by at least 15 serial passages in susceptible tissue culture to render the virus non-pathogenic without loss of immunogenicity.

18. A method of immunizing dogs against kennel cough which comprises parenterally or intranasally administering to a susceptible dog from about $10^5$ to about $10^9$ inactivated *Bordetella bronchisepticus* bacteria per ml and from about $10^4$ to about $10^6$ $TCID_{50}$ per ml of live attenuated canine parainfluenza virus in a physiologically acceptable carrier, said virus being attenuated by from about 20 to about 45 serial passages in canine kidney tissue culture to render the virus non-pathogenic without loss of immunogenicity.

19. A vaccine useful in immunizing dogs against kennel cough comprising at least 100 $TCID_{50}$ per ml of live attenuated canine parainfluenza virus in a physiologically acceptable carrier suitable for parenteral or intranasal administration, said virus being attenuated by a sufficient number of serial passages in susceptible tissue culture until the virus is rendered non-pathogenic without loss of immunogenicity.

20. A vaccine useful in immunizing dogs against kennel cough comprising from about $10^4$ to about $10^6$ $TCID_{50}$ per ml of live attenuated canine parainfluenza virus in a physiologically acceptable carrier suitable for parenteral or intranasal administration, said virus being attenuated by at least 15 serial passages in susceptible tissue culture to render the virus non-pathogenic without loss of immunogenicity.

21. A vaccine useful in immunizing dogs against kennel cough comprising from about $10^4$ to about $10^6$ $TCID_{50}$ per ml of live attenuated canine parainfluenza virus in a physiologically acceptable carrier suitable for parenteral or intranasal administration, said virus being attenuated by from about 20 to about 45 serial passages in canine kidney tissue culture to render the virus non-pathogenic without loss of immunogenicity.

22. A method of immunizing dogs against kennel cough which comprises parenterally or intranasally administering to a susceptible dog at least 100 $TCID_{50}$ per ml of live attenuated canine parainfluenza virus in a physiologically acceptable carrier, said virus being attenuated by a sufficient number of serial passages in susceptible tissue culture until the virus is rendered non-pathogenic without loss of immunogenicity.

23. A method of immunizing dogs against kennel cough which comprises parenterally or intranasally administering to a susceptible dog from about $10^4$ to about $10^6$ $TCID_{50}$ per ml of live attenuated canine parainfluenza virus in a physiologically acceptable carrier, said virus being attenuated by at least 15 serial passages in susceptible tissue culture to render the virus non-pathogenic without loss of immunogenicity.

24. A method of immunizing dogs against kennel cough which comprises parenterally or intranasally administering to a susceptible dog from about $10^4$ to about $10^6$ $TCID_{50}$ per ml of live attenuated canine parainfluenza virus in a physiologically acceptable carrier, said virus being attenuated by from about 20 to about 45 serial passages in canine kidney tissue culture to render the virus non-pathogenic without loss of immunogenicity.

\* \* \* \* \*

Disclaimer 3,950,512.—*Jerrell Bemis Emery*, Chalfont, and *James Long Bittle*, Doylestown, Pa. ANIMAL VACCINES. Patent dated Apr. 13, 1976. Disclaimer filed May 9, 1978, by the assignee, *Pitman-Moore, Incorporated*.

Hereby enters this disclaimer to claims 2, 3, 5, 6, 8, 9, 11, 12, 14, 15, 17, 18, 20 and 21 of said patent.

[*Official Gazette July 25, 1978.*]